US00PP34934P2

(12) United States Plant Patent
NeSmith

(10) Patent No.: US PP34,934 P2
(45) Date of Patent: Jan. 24, 2023

(54) SOUTHERN HIGHBUSH BLUEBERRY PLANT NAMED 'TO-1719'

(50) Latin Name: *Vaccinium corymbosum*
Varietal Denomination: TO-1719

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/862,795

(22) Filed: Jul. 12, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Karen M Redden
(74) *Attorney, Agent, or Firm* — Thomas Horstemeyer, LLP

(57) ABSTRACT

A new and distinct cultivar of *Vaccinium* plant named 'TO-1719', characterized by a combination of early to mid-season ripening and flowering, large, firm berries with good color, and mild sweet and acid flavor; and a chill requirement of about 350 to 450 hours, or more, below about 45° F.

6 Drawing Sheets

Botanical designation: *Vaccinium corymbosum.*
Cultivar denomination 'TO-1719'.

BACKGROUND OF THE INVENTION

The present invention relates to a new and distinct cultivar of southern highbush blueberry plant, botanically know as *Vaccinium corymbosum*, and hereinafter referred to by the cultivar name 'TO-1719'.

The new *Vaccinium corymbosum* 'TO-1719' was first identified and selected by the inventor in 2012 in Griffin, Ga. The new variety 'TO-1719' is early to mid-season for flowering time and ripening. 'TO-1719'. 'TO-1719' has large berries with good color and flavor as compared to other early season varieties. 'TO-1719' produces high quality, flavorful fruit when grown in conventional production areas. The new variety is estimated to have a chilling requirement of about 350-450 hours, or more, below 45° F. when produced under typical low to mid chill production areas in temperate regions. 'TO-1719' is able to produce high-quality fruit when grown in conventional production areas and is being released primarily for home garden usage.

'TO-1719' was produced from seedlings derived from an open-pollinated cross of *Vaccinium corymbosum* 'TH-749' (female parent, non-patented breeding line) X unknown male parent. Seeds from the cross were collected in 2010 by D. Scott NeSmith. Seeds were planted in 2010, and new seedlings 'TO-1719' were identified in 2012. 'TO-1719' has been tested in asexually propagated (by softwood vegetative cuttings) plantings in Alapaha, Ga. since 2014 where it was established for testing comparing to industry standards. Observations of the resulting 'TO-1719' progeny have shown that the unique features of this new *Vaccinium corymbosum* 'TO-1719' are stable and reproduced true to type in successive generations.

SUMMARY OF THE INVENTION

The new *Vaccinium* cultivar 'TO-1719' has not been observed under all possible environmental conditions. The phenotype may vary somewhat with variations in environment and cultural practices such as temperature, water and fertility levels, soil types, and light intensity without, however, any variance in genotype.

The following traits have been consistently observed and are determined to be the unique and distinguishing characteristics of the new *Vaccinium corymbosum* cultivar named 'TO-1719'. In combination, these traits set 'TO-1719' apart from all other existing varieties of southern highbush blueberry known to the inventors:

1. early to mid-season, flowering around the same time as and ripening later than 'Suziblue' (U.S. Plant Pat. No. 21,167), and 'Rebel' (U.S. Plant Pat. No. 18,138) (Table 1);
2. producing large berries with lighter color and mildly sweet and acid flavor as compared to 'Suziblue' and 'Rebel'; and
3. medium chilling requirement of 350 to 450 hours, or more, below 45° F. (based on comparison of flowering dates with those of known standard cultivars) when produced under typical low to mid chill production regions.

As compared to female parent 'TH-749', plants of *Vaccinium* 'TO-1719' have a higher chilling requirement, later ripening times, similar berry size and scar, and are less firm, but have a better color rating and similar flavor rating. The chilling requirement for 'TO-1719' (at about 350-450 hours) is higher than 'TH-749' (at about 250 to 350 hours). 'TO-1719' flowering and ripening times are 5 to 8 days later than 'TH-749'. Firmness for 'TO-1719' (7.0/10) is less than that of 'TH-749' (7.8/10). 'TO-1719' berry color rating (8.0/10) is higher than that of 'TH-749' (7.0/10); whereas berry flavor rating for 'TH-749' (8.0/10) is slightly higher than that of 'TO-1719' (7.5/10).

Plants of the new *Vaccinium* 'TO-1719' can also be compared to the commercial early season southern highbush blueberry cultivars 'Suziblue' and 'Rebel' as shown in Table 1. The new variety 'TO-1719' is early season and begins flowering around the same time as 'Suziblue' and 'Rebel' and ripening slightly later. Berry size is smaller than 'Suziblue' and about the same as 'Rebel' with similar scar and firmness. 'TO-1719' has a higher color rating (lighter color) and flavor rating (well-balanced sweetness to acidity) than both 'Suziblue' and 'Rebel'. No notable diseases or other pest problems have been observed for the new variety that are not also common for other varieties. The new variety is estimated to have a chilling requirement of about 350-450 hours, or more, below about 45° F. (based on comparison of flowering dates with those of known standard cultivars) when produced under typical low to mid chill production regions. Additional comparison data of 'TO-1719' with 'Suziblue' and 'Rebel' are presented in the tables below.

Table 1. Plant and fruit ratings for 'TO-1719' and two standards in Alapaha, Ga. Data represents a 3 year average (2015, 2016, and 2021). Rating scales are based on a 1 to 10 score, with 1 being the least desirable and 10 being the most desirable. Plants were established in 2014.

TABLE 1

Plant and fruit ratings for 'TO-1719' and two standards in Alapaha, GA. Data represents a 3 year average (2015, 2016, and 2021). Rating scales are based on a 1 to 10 score, with 1 being the least desirable and 10 being the most desirable. Plants were established in 2014.

| | 'Suizblue' | 'Rebel' | 'TO-1719' |
|---|---|---|---|
| Berry size | 8.2 | 7.8 | 7.5 |
| Berry scar | 7.3 | 7.0 | 7.5 |
| Berry color | 7.2 | 7.2 | 8.0 |
| Berry firmness | 7.5 | 7.0 | 7.0 |
| Berry flavor | 7.2 | 6.0 | 7.5 |
| Cropping | 7.0 | 5.0 | 7.0 |
| Plant vigor | 8.5 | 7.5 | 7.0 |
| Date of 50% flowering | March 6 | March 4 | March 8 |
| Date of 50% ripening | May 7 | May 4 | May 16 |
| Fruit development period (days) | 62 | 60 | 69 |

BRIEF DESCRIPTION OF THE DRAWINGS

The accompanying colored photographic illustrations show the overall appearance and distinct characteristics of the new cultivar of *Vaccinium corymbosum* 'TO-1719' showing the colors as true as possible. Colors in the photographs may differ slightly from the color values cited in the detailed botanical description, which accurately describes the colors of the new *Vaccinium corymbosum* 'TO-1719'. Photographs were taken of plants grown outdoors in Alapaha, Ga. during different years.

The photograph labeled

The photograph labeled

The photograph labeled

The photograph labeled

The photographs labeled FIG. 5A is a close-up view of fruit of 'TO-1719' in a plastic container, and FIG. 5B shows a cross sectional view of the interior of the fruit taken in May 2021.

The photograph labeled

DETAILED BOTANICAL DESCRIPTION

Figure 1:
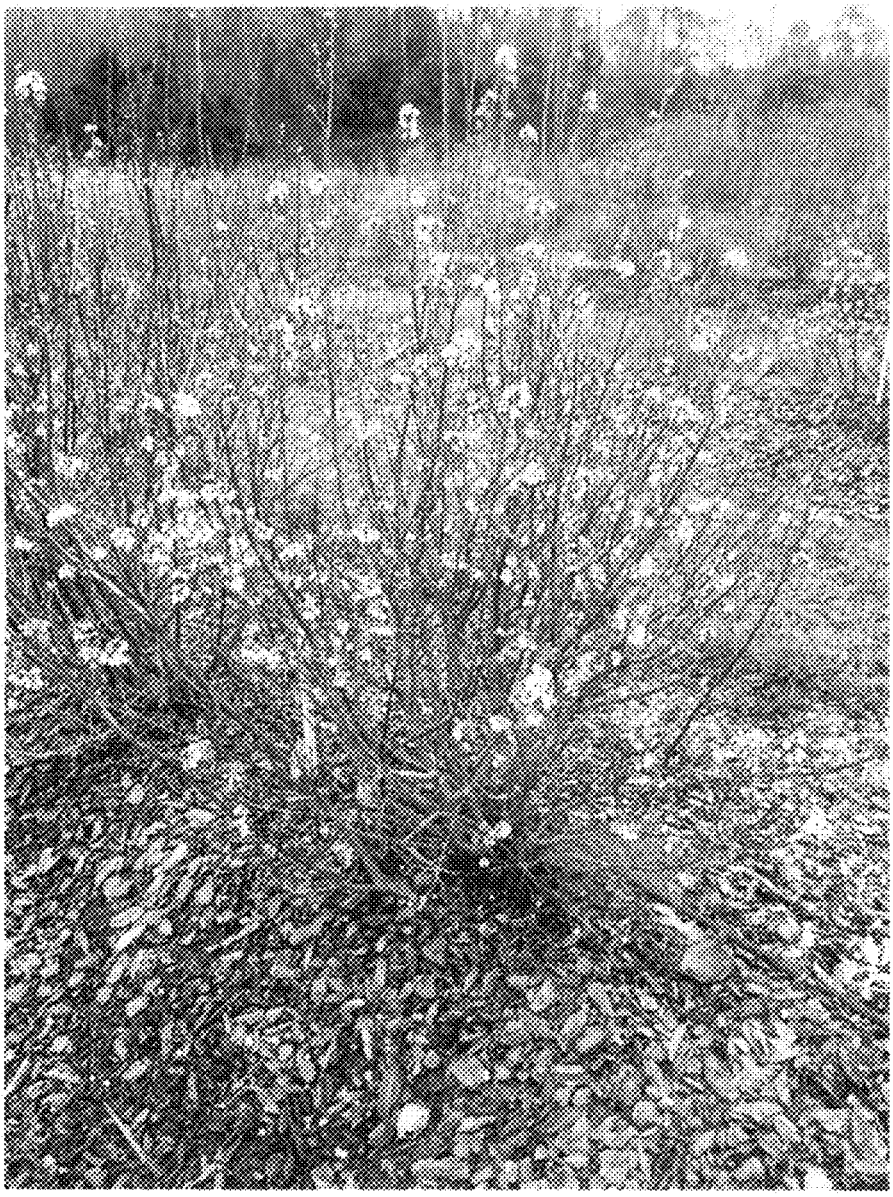
FIG. 1 depicts 'TO-1719' plants during flowering. Plants are 3 years old, and photo was taken in March 2021 at Alapaha, Ga.
Figure 2:
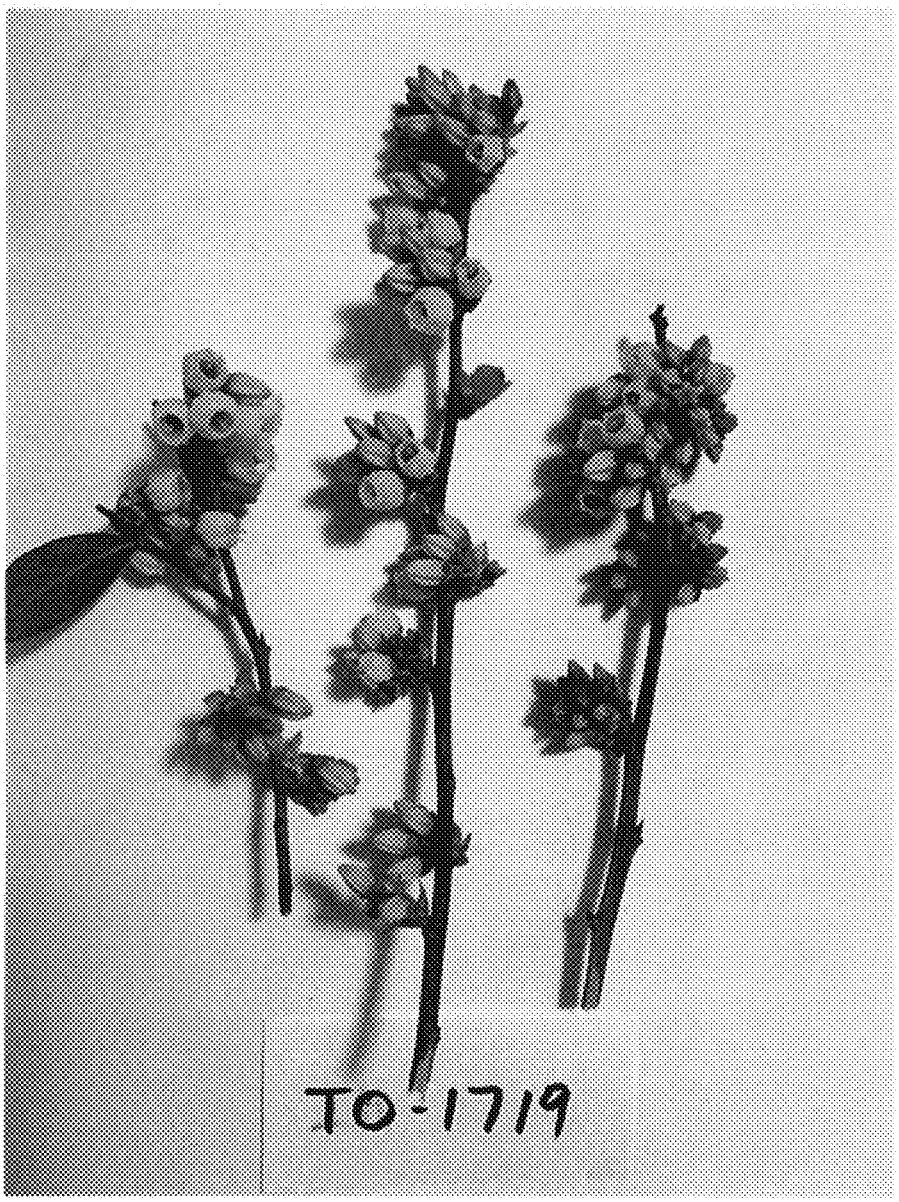
FIG. 2 depicts a close-up of 'TO-1719' flowering branches. Photo was taken in March 2021 at Alapaha, Ga.
Figure 3:
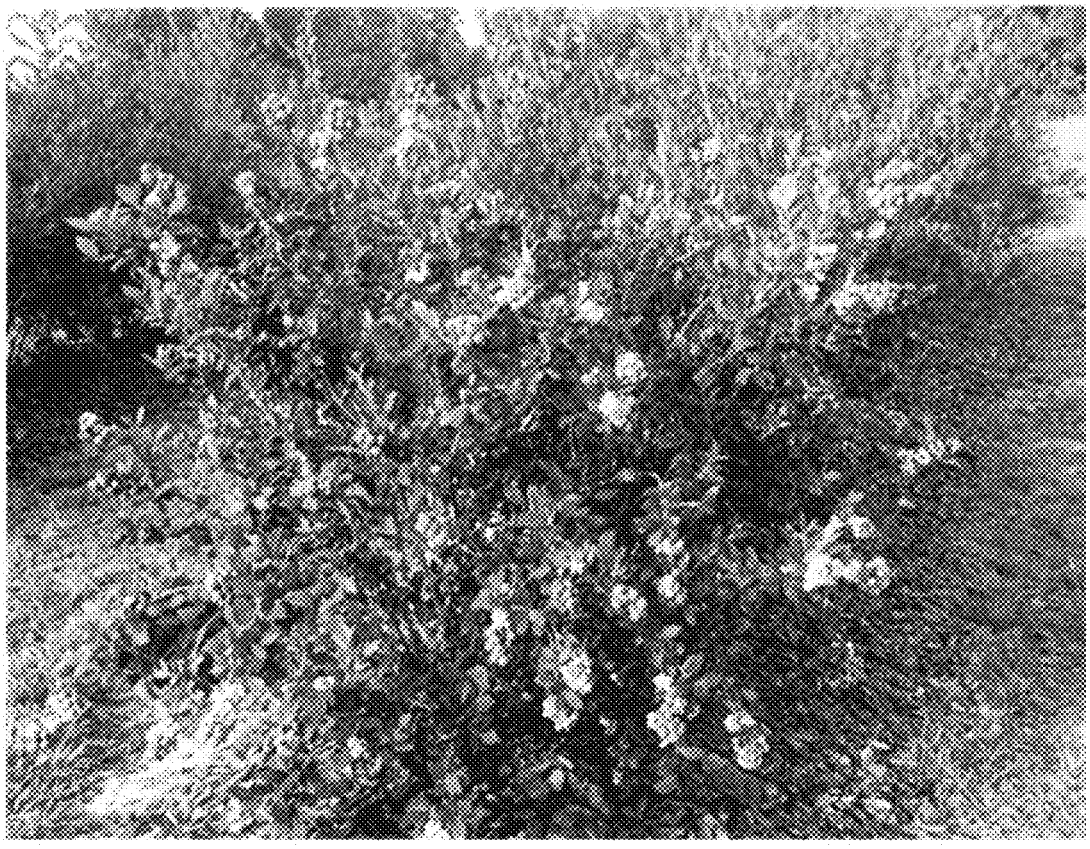
FIG. 3 depicts mature plants of 'TO-1719' during fruit ripening. Plants are 3 years old, and photo was taken in May 2021 at Alapaha, Ga.
Figure 4:
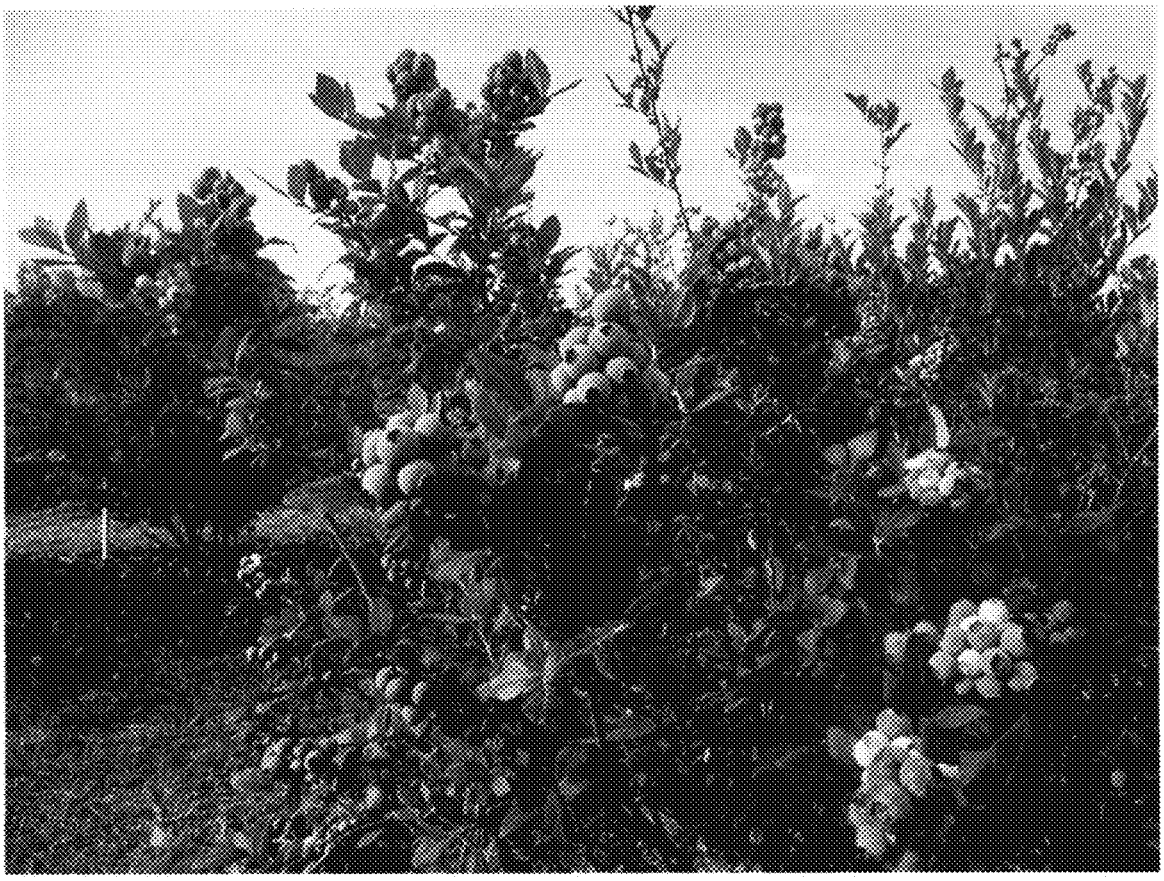
FIG. 4 depicts a close-up view of 'TO-1719' fruit on the plant. Plants are 3 years old and photo was taken in May 2021 at Alapaha, Ga.
Figure 5A:
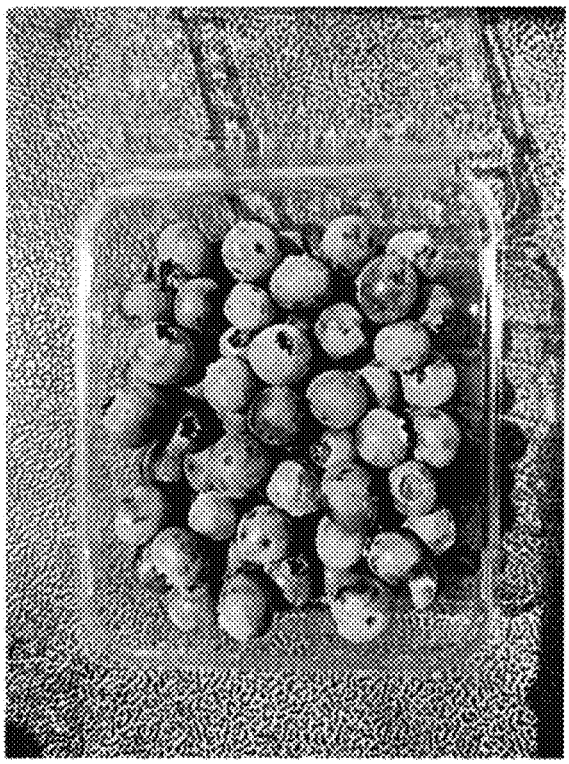
FIGS. 5A-5B depict close-up views of 'TO-1719' fruit.
Figure 5B:
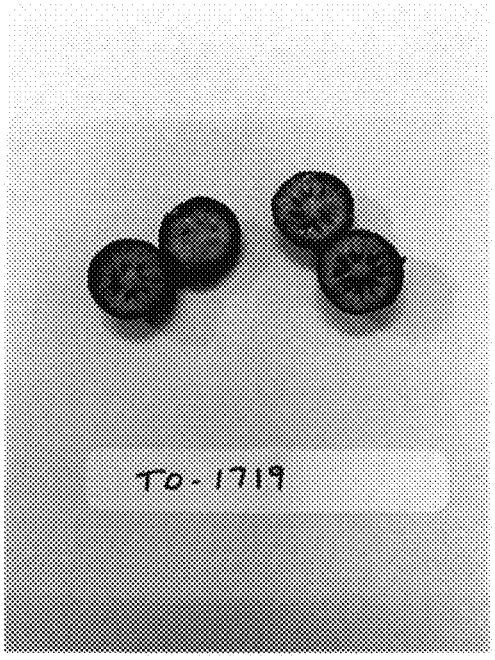
Figure 6:
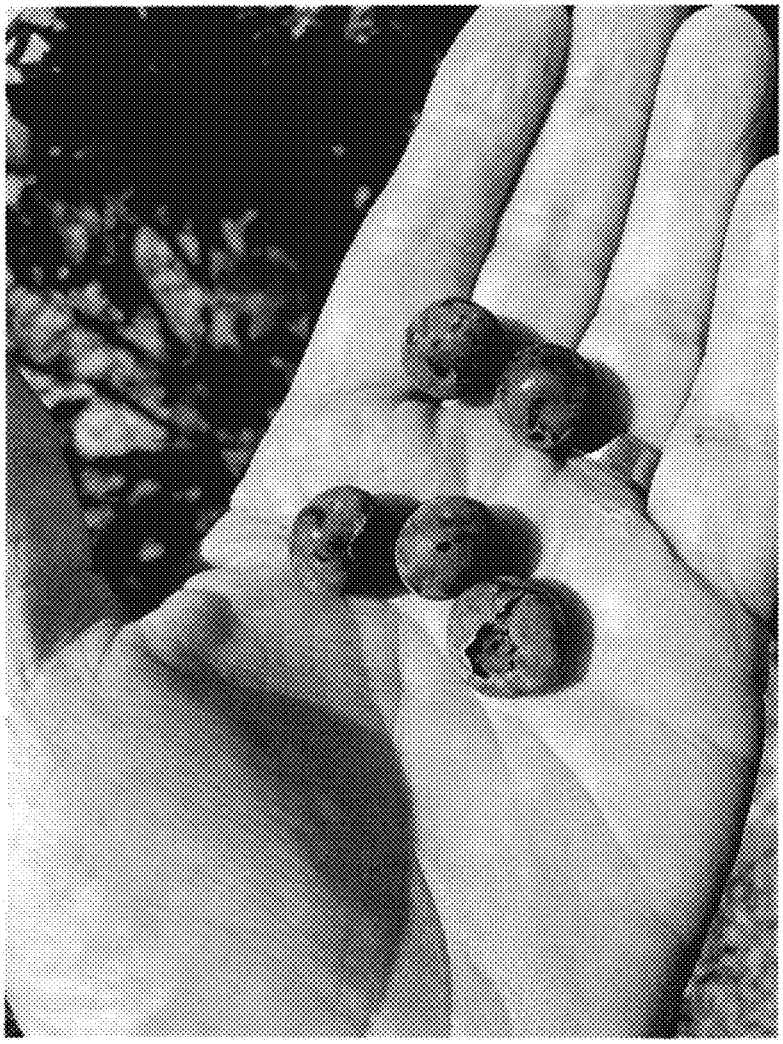
FIG. 6 depicts a close-up view of 'TO-1719' fruit in a human hand, illustrating the relative size of the fruit taken in May 2021.

The following is a detailed description of the botanical and pomological characteristics of the subject blueberry clone. The following traits have been consistently observed in the original plant of this new variety and in asexually propagated progeny grown in Alapaha and Griffin, Ga., and, to the best knowledge of the inventors, their combination forms the unique characteristics of the new variety *Vaccinium corymbosum* 'TO-1719'.

Throughout this specification, color names beginning with a small letter signify that the name of that color, as used in common speech, is aptly descriptive. Color names beginning with a capital letter designate values based upon The R.H.S. Colour Chart, $5^{th}$ edition published by the Royal Horticultural Society, London, England in 2007, except where general terms of ordinary dictionary significance are used.

The aforementioned photographs and following observations, measurements, and values describe plants of the *Vaccinium corymbosum* cultivar named 'TO-1719'. Where dimensions, sizes, colors, and other characteristics are given, it is to be understood that such characteristics are approximations and averages set forth as accurately as practicable. Data were collected between the years of 2016-2021 from a farm in Alapaha, Ga. from 3 to 4-year-old plants (planted in the field with supplemental irrigation). In this region, the long-term average annual low temperature ranges from about 54° F. to 58° F., and the average annual high temperature for the year ranges from about 78° F. to 82° F.

Botanical classification: *Vaccinium corymbosum* 'TO-1719'.

*Commercial classification.*—Fruit-bearing shrub.

*Parentage.*—Originated from seeds collected from open-pollinated fruit of 'TH-749' (non-patented breeding line).

Growth and propagation:

*Propagation type.*—Vegetative by softwood cuttings.

*Growth rate.*—Plant vigor is medium, canopy tends to stay compact.

*Root description.*—Fibrous.

Plant description:

*Size of plant.*—Plant is about 1.2 to 1.4 m tall by about 4 years. The plant crown, or base, is medium, typically about 20 to 30 cm in diameter. Upper portion of plant canopy reaches about 1.2 to 1.5 m in diameter by about 4 years.

*Growth habit.*—Plant has a candelabra growth habit that is semi-spreading, yet canes turn quickly upright. Three to 5 main canes arising from crown with multiple branching of shoots from those canes about 10 to 15 cm above ground.

*Growth.*—Plants are moderately vigorous, but remain compact, with a somewhat dense canopy.

*Productivity*.—Medium to high yielding. Yields of about 5 to 8 lbs. per plant each year on plants 4-years old or older grown under well fertilized and irrigated field conditions.

*Cold hardiness*.—Similar to other early ripening southern highbush varieties such as Suziblue (U.S. Plant Pat. No. 21,167) and Rebel (U.S. Plant Pat. No. 18,138).

*Disease resistance*.—No exceptional disease resistance or susceptibility observed. Typical for early season southern highbush such as 'Suziblue' and 'Rebel'.

*Chilling requirement*.—Plants are medium chill, requiring an estimated 350 to 450 hours, or more, of temperatures at or below 45° F. (7° C.) to induce normal leafing and flowering during the spring under conventional dormant production systems. The chill requirement is somewhat more than the female parent 'TH-749' (250 to 350 hours of chilling required). The male parent is unknown.

*Leafing*.—Plants tend to break sufficient leaf buds simultaneously with, or shortly after, anthesis.

*Canes*.—Main cane base diameter is about 15 to 25 mm, color most near Brown N200C; two year old cane diameter 10 to 15 mm, color transitioning from Yellow Green 145B to Greyed Orange 165A; current season wood diameter 3 to 8 mm, color Yellow Green 145A.

*Fruiting wood*.—Moderate number of twigs (about 10 to 15 common) of about 10 to 25 cm in length, with internode lengths of about 15 to 25 mm common. Plants flower and fruit on one-year-old shoots.

Foliage:

*Leaf color*.—Healthy mature leaves.—top side of leaf color is Green N137C, under side of leaf color is Green N138C to Green 138B.

*Leaf arrangement*.—Alternate, simple.

*Leaf shape*.—Nearly elliptic.

*Leaf margins*.—Slight serration on young leaves transitioning to nearly entire as leaves mature.

*Leaf venation*.—Pinnate with slight netting.

*Leaf apices*.—Acuminate.

*Leaf bases*.—Acute.

*Leaf dimensions*.—Length: about 40 to 55 mm; width: about 20 to 30 mm.

*Petioles*.—Small, about 1.0 to 3.0 mm long, about 1.5 to 2.0 mm wide; Color: Yellow Green 145C.

*Texture*.—Both upper and lower leaf surfaces glaucous.

Flowers:

*Date of* 50% *anthesis*.—3-year average March 8 in southeast Georgia.

*Flower shape*.—Urceolate.

*Flower bud number*.—High to very high, averaging 5 to 8 buds per fruiting shoot.

*Flower bud anthocyanin coloration*.—Medium.

*Flowers per cluster*.—About 6 to 9 common.

*Flower fragrance*.—None detected.

*Corolla color*.—White NN 155C once fully expanded (open).

*Corolla length*.—About 6.5 to 8.0 mm.

*Corolla width*.—About 6.5 to 7.5 mm.

*Corolla aperture width*.—About 4.0 to 5.0 mm.

*Flower peduncle*.—Length about 7.0 to 10.0 mm; Color: Green 138D.

*Flower pedicel*.—Length about 2.5 to 3.5 mm; Color: Green 138C.

*Calyx* (*with sepals*).—Diameter: about 6.5 to 7.5 mm; Color: sepals Green 138D; calyx center Green 138C.

*Stamen*.—Length: about 5.5 to 6.5 mm; number per flower: about 10; filament color: Green White 157C.

*Style*.—Length: about 7.5 to 8.5 mm; Color: Yellow Green 145B.

*Pistil*.—Length: about 9.5 to 10.5 mm; ovary color: Green 138C.

*Anther*.—Length: about 3.5 to 4.5 mm; number: 10; Color: Greyed Orange 165B.

*Pollen*.—Abundance: high; Color: Yellow White 158A.

*Compatibility*.—The cultivar has a moderate degree of self-compatibility.

Fruit:

*Date of* 50% *maturity*.—3-year average around May 16 in southeast Georgia.

*Fruit development period*.—About 69 days in southeast Georgia.

*Berry color*.—With wax Violet Blue 98D; with wax removed Black 203C.

*Berry flesh color*.—Green White 157C.

*Berry surface wax abundance*.—High.

*Berry weight*.—1st harvest: about 2.0 to 2.5 g; 2nd harvest about 1.6 to 2.1 g.

*Berry size*.—Height from calyx to scar: about 15 to 17 mm; diameter: about 17 to 19 mm.

*Berry shape*.—Nearly spherical shape.

*Fruit stem scar*.—Small to medium, dry, with little or no tearing upon harvest.

*Fruit calyx*.—Depth about 1.0 to 3.0 mm; width about 5.0 to 7.0 mm; sepals most often present, turned mostly inwards and upward when present, length about 1.0 to 2.0 mm.

*Berry firmness*.—Medium to high firmness.

*Berry flavor and texture*.—Mildly sweet and acid flavor; texture is smooth.

*Storage quality*.—Fair to good.

*Suitability for mechanical harvesting*.—Not likely suitable.

*Uses*.—Primarily to be used in home garden market.

Seed:

*Seed abundance in fruit*.—High, typically with 15 to 20 or more fully developed seeds per berry.

*Seed color*.—Greyed Orange 166C.

*Seed dry weight*.—50.4 mg per 100 seed.

*Seed size*.—1.5 to 2.0 mm long.

It is claimed:

1. A new and distinct cultivar of the *Vaccinium* plant named 'TO-1719' as illustrated and described herein.

* * * * *